(12) United States Patent
Suzuki

(10) Patent No.: US 9,237,884 B2
(45) Date of Patent: Jan. 19, 2016

(54) TREATMENT DEVICE FOR ENDOSCOPE

(71) Applicant: OLYMPUS MEDICAL SYSTEMS CORP., Tokyo (JP)

(72) Inventor: Keita Suzuki, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/523,231

(22) Filed: Oct. 24, 2014

(65) Prior Publication Data
US 2015/0105692 A1 Apr. 16, 2015

Related U.S. Application Data

(63) Continuation of application No. PCT/JP2013/070048, filed on Jul. 24, 2013.

(60) Provisional application No. 61/682,579, filed on Aug. 13, 2012.

(51) Int. Cl.
*A61B 5/00* (2006.01)
*A61B 10/04* (2006.01)
(Continued)

(52) U.S. Cl.
CPC .............. *A61B 10/04* (2013.01); *A61B 10/0275* (2013.01); *A61B 10/06* (2013.01); *A61B 2010/045* (2013.01); *A61B 2017/320791* (2013.01)

(58) Field of Classification Search
CPC ............... A61B 10/02; A61B 10/0233; A61B 10/0266; A61B 10/0275; A61B 10/06; A61B 10/04
USPC ................................................ 600/562–567
See application file for complete search history.

(56) References Cited

U.S. PATENT DOCUMENTS 5,301,684 A * 4/1994 Ogirala ..................... 600/567
6,638,233 B2 * 10/2003 Corvi et al. ............... 600/564
(Continued)

FOREIGN PATENT DOCUMENTS

JP U-54-63990 5/1979
JP U-54-63989 5/1989
(Continued)

OTHER PUBLICATIONS

International Search Report issued in International Application No. PCT/JP2013/070048 mailed Sep. 24, 2013 (with translation).
Office Action issued in Japanese Application No. 2014-501115 mailed Jul. 8, 2014 (with translation).
(Continued)

*Primary Examiner* — Max Hindenburg
(74) *Attorney, Agent, or Firm* — Oliff PLC

(57) ABSTRACT

An endoscopic treatment device includes: an elongated needle pipe having flexibility; a hollow shape section having an inner cavity formed in a distal end section of the needle pipe, and a side hole formed on an outer side surface of the needle pipe and communicating with the inner cavity; a piercing section provided closer to a distal end side of the needle pipe than the hollow shape section and formed with a pointed tip; a collection member including a cutting edge section having a pointed shape toward a radial outer direction of the needle pipe and protruding and retracting between a position where the cutting edge section is housed in the hollow shape section and a position where the cutting edge section protrudes from the side hole; and an operating member advanceable and retractable relative to the needle pipe and including a distal end portion connected to the collection member.

6 Claims, 14 Drawing Sheets

(51) Int. Cl.
*A61B 10/02* (2006.01)
*A61B 17/3207* (2006.01)
*A61B 10/06* (2006.01)

(56) References Cited

U.S. PATENT DOCUMENTS 7,762,960 B2 * 7/2010 Timberlake et al. .......... 600/564
7,775,989 B2 * 8/2010 Nakao ........................... 600/564

FOREIGN PATENT DOCUMENTS

| | | |
|---|---|---|
| JP | U-1-133907 | 9/1989 |
| JP | A-5-237120 | 9/1993 |
| JP | A-11-128234 | 5/1999 |
| JP | A-2001-61846 | 3/2001 |
| JP | A-2007-289673 | 11/2007 |
| JP | A-2010-274128 | 12/2010 |

* cited by examiner

TREATMENT DEVICE FOR ENDOSCOPE

This application is a continuation application based on a PCT Patent Application No. PCT/JP2013/070048, filed Jul. 24, 2013, whose priority is claimed on US Provisional Patent Application No. 61/682,579, filed on Aug. 13, 2012. The contents of both the PCT Patent Application and the US Provisional Patent Application are incorporated herein by reference.

BACKGROUND OF THE INVENTION

1. Field of the Invention

The present invention relates to a treatment device for an endoscope and, more particularly, to a treatment device for an endoscope capable of piercing tissue to collect tissue for a biopsy.

2. Description of Related Art

As one of conventional treatment devices for an endoscope, a treatment device for piercing tissue to collect a part of the tissue for a biopsy has been known. Such a treatment device for an endoscope is called a biopsy needle or a biopsy tool.

For example, a biopsy tool having a cup is described in Japanese Unexamined Patent Application, First Publication No. H11-128234. The cup is provided at a distal end section of a long inserting section inserted into a human body, and functions as a tissue collecting section. A proximal end side of the cup is provided with a bendable direction-adjusting mechanism having joints.

Further, a biopsy tool having a forceps cup is described in Japanese Unexamined Patent Application, First Publication No. 2007-289673. A needle section is formed at a distal end of the forceps cup, and can be opened or closed. The forceps cup is opened or closed by advance or retraction of an operating wire.

SUMMARY OF THE INVENTION

According to a first aspect of the present invention, a treatment device for an endoscope includes: a needle pipe having flexibility and formed in an elongated shape; a hollow shape section having an inner cavity formed in a distal end section of the needle pipe, and a side hole that is formed on an outer side surface of the needle pipe and communicates with the inner cavity; a piercing section provided closer to a distal end side of the needle pipe than the hollow shape section and formed with a pointed tip; a collection member including a cutting edge section that is formed in a pointed shape toward a radial outer direction of the needle pipe and is configured to protrude and retract between a position at which the cutting edge section is housed in the hollow shape section and a position at which the cutting edge section protrudes from the side hole; and an operating member including a distal end portion connected to the collection member, the operating member being provided so as to be advanceable and retractable relative to the needle pipe. The cutting edge section protrudes from the side hole when the operating member is displaced relative to the needle pipe.

According to a second aspect of the present invention, in first aspect, the collection member may include a cup section having an opening to a storage space capable of storing tissue therein. The cutting edge section may be formed in a periphery of the opening. The opening may open toward the side hole in a state in which the cup section is housed in the hollow shape section.

According to a third aspect of the present invention, in the first aspect, the collection member may be mounted in the needle pipe via a rotation shaft, and be rotatable around the rotation shaft.

According to a fourth aspect of the present invention, the treatment device according to the first aspect may further include: a sheath into which the needle pipe is inserted so as to be advanceable and retractable; and an outer blade provided at a distal end section of the sheath and configured to cut tissue collected by the collection member.

According to a fifth aspect of the present invention, in the third aspect, the collection member may include a first cup section, which is mounted in the needle pipe via the rotation shaft and is rotatable around the rotation shaft, at a first end of the collection member in a longitudinal direction of the collection member, and a middle section of the collection member in the longitudinal direction may be supported on the rotation shaft. When the operating member is retracted relative to the needle pipe, a second end of the collection member in the longitudinal direction may protrude from a second side hole formed in the needle pipe.

According to a sixth aspect of the present invention, in the fifth aspect, the collection member may further include a second cup section that is provided at the second end of the collection member and opens toward a radial outer side of the needle pipe.

According to a seventh aspect of the present invention, the treatment device according to the third aspect may further include a link that connects the collection member and the operating member.

According to an eighth aspect of the present invention, the treatment device according to the second aspect may further include a cutting section which is provided in the needle pipe and with which the rotated cup section comes into contact.

DETAILED DESCRIPTION OF THE INVENTION

First Embodiment

Hereinafter, a first embodiment of the present invention will be described with reference to FIGS. 1 to 3.

Figure 1:
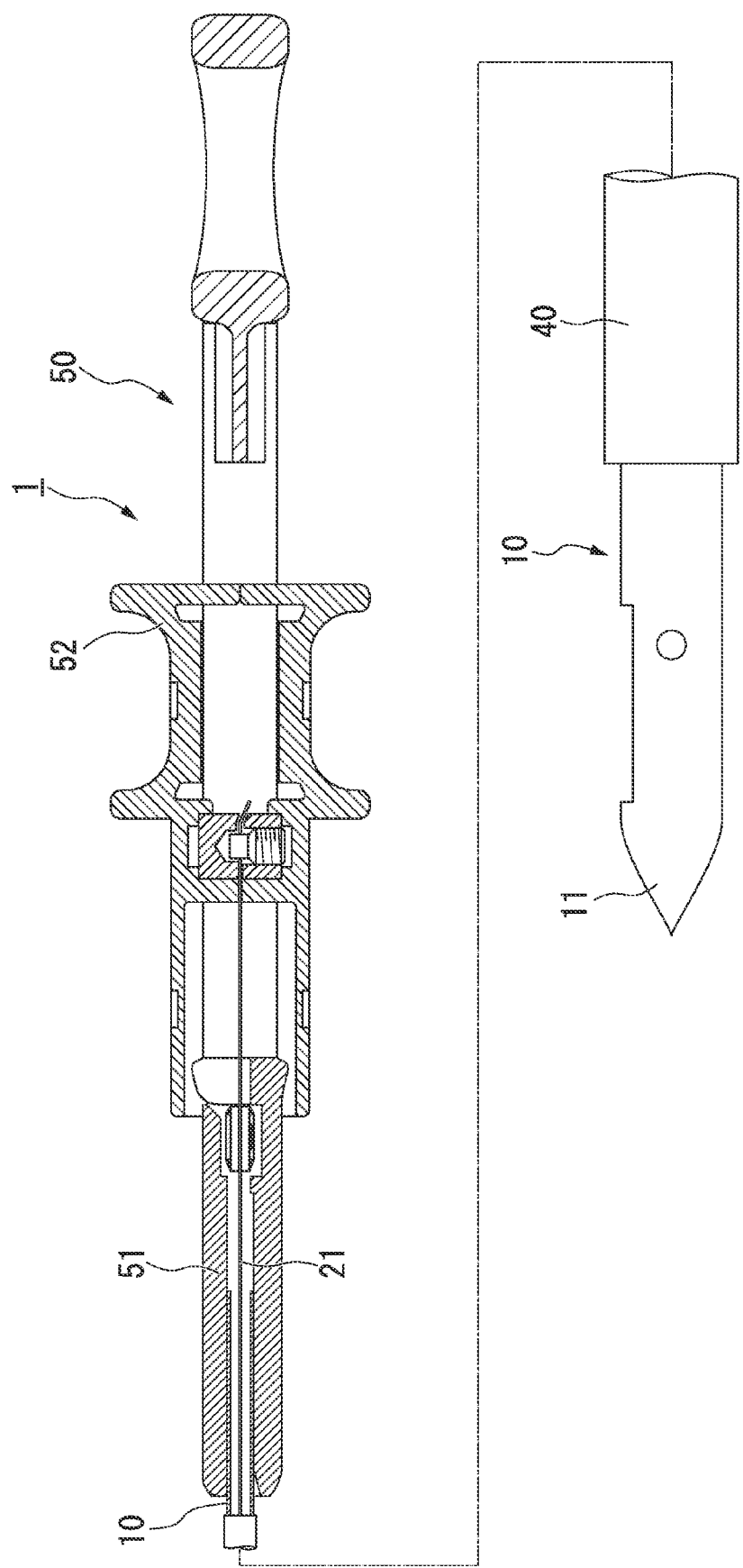
FIG. 1 is a view showing an entire constitution of a biopsy needle that is a treatment device for an endoscope of a first embodiment of the present invention.

FIG. 1 is a view showing an entire constitution of a biopsy needle 1 that is a treatment device for an endoscope of the present embodiment. The biopsy needle 1 includes a long needle pipe 10 having flexibility, a sheath 40 into which the needle pipe 10 is inserted so as to be advanceable or retractable, and an operating section 50 mounted on a proximal end section of the needle pipe 10.

The needle pipe 10 is formed of a metal such as stainless steel in a hollow shape having an inner cavity, but has flexibility due to a small outer diameter of, for instance, about 0.5 to 2 millimeters (mm). A distal end section of the needle pipe 10 is formed in a conical shape. The conical distal end section is a sharp piercing section 11 that is inserted into tissue to be biopsied.

Figure 2:
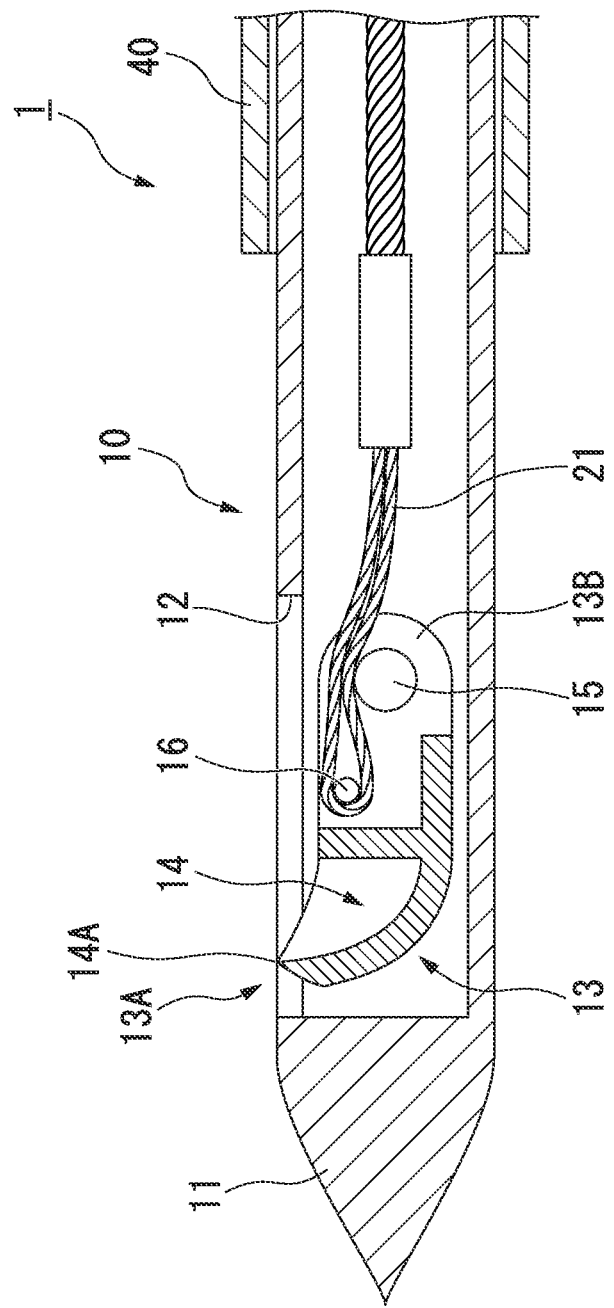
FIG. 2 is a cross-sectional view of a distal end of a needle pipe and surroundings thereof in the biopsy needle.
Figure 3:
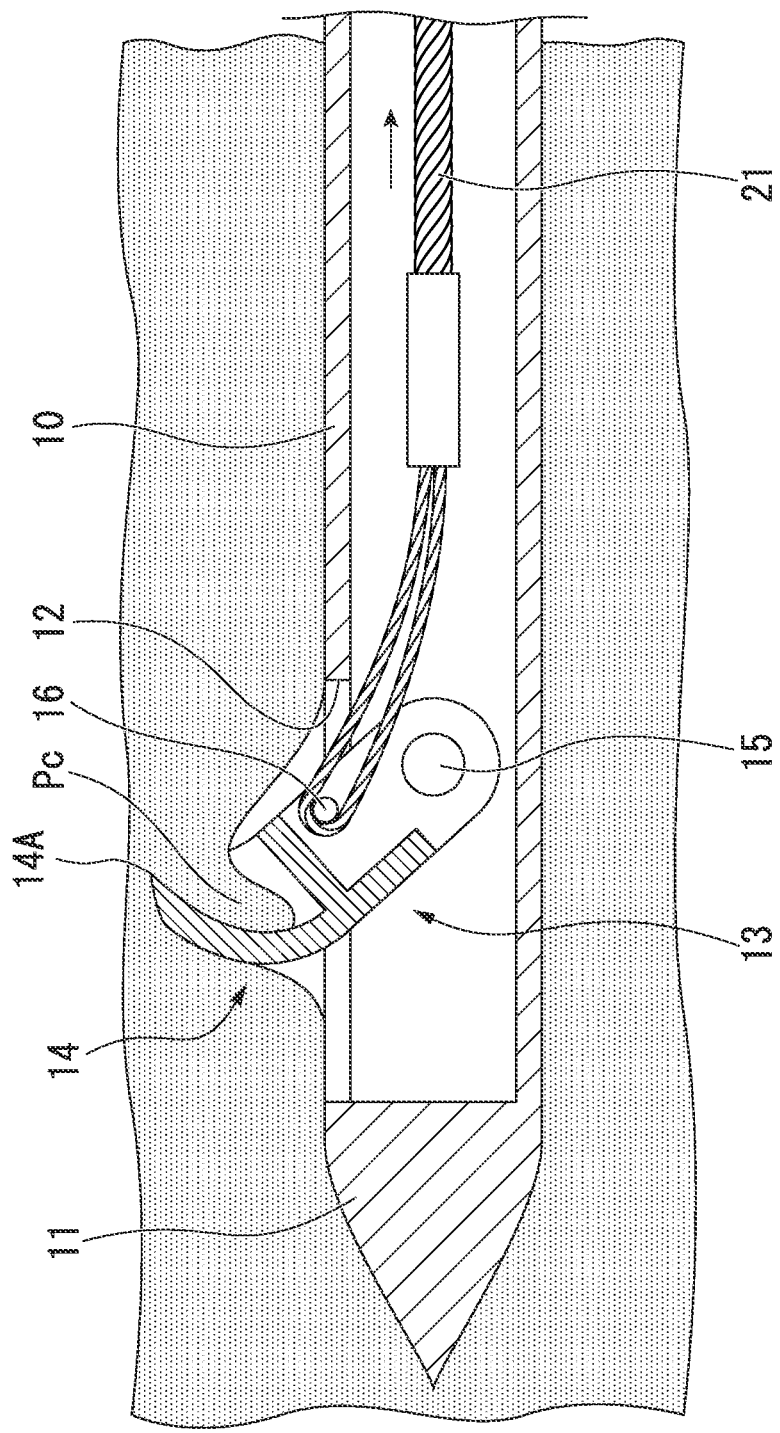
FIG. 3 is a view showing an operation of the biopsy needle in use.

FIG. 2 is a cross-sectional view of the distal end section of the needle pipe 10 and surroundings thereof. An outer circumferential surface of the needle pipe 10 is provided with a side hole 12 communicating with the inner cavity. A collection member 13 configured to collect tissue is disposed in the inner cavity of the needle pipe 10. A first end 13A of the collection member 13 is provided with a cup section 14 having a storage space in which the collected tissue is stored. A periphery 14A of the cup section 14 which becomes an opening of the storage space has the shape of a sharp cutting edge, and can easily resect the tissue.

As shown in FIG. 2, a second end 13B of the collection member 13, which is located on the opposite side of the first end 13A, is supported by a rotation shaft 15 mounted to pass through the needle pipe 10 in a radial direction, and is rotatable around the rotation shaft 15. The collection member 13 is mounted such that the first end 13A in which the cup section 14 is provided is at the side of the piercing section 11, and an opening of the cup section 14 is directed to a radial outer side of the needle pipe 10 and the side of the side hole 12.

In the collection member 13, an operating wire (operating member) 21 for operating the collection member 13 is connected to a middle side between the cup section 14 and the rotation shaft 15. In the present embodiment, the operating wire 21 is fixed and connected to a pin 16 provided in the collection member 13. However, the connection mode is not limited thereto, and the operating wire 21 may be connected by another method, such as, for example, welding. The operating wire 21 extends up to an operating section 50 through the inner cavity of the needle pipe 10, and can be advanced or refracted relative to the needle pipe 10.

The sheath 40 only needs to have flexibility and allow the needle pipe 10 to be inserted thereinto so as to be advanceable or retractable, and a known sheath may be appropriately selected and used. There is no particular limitation to a material. For example, a variety of known materials such as a resin and a coil may be used.

As shown in FIG. 1, the operating section 50 includes an operating section body 51 fixed to a proximal end section of the needle pipe 10, and a slider 52 mounted to be slidable in a longitudinal direction of the operating section body 51, and a basic constitution thereof is known. A proximal end section of the operating wire 21 extending through the inside of the needle pipe 10 protrudes to an internal space of the operating section body 51, and is fixed to the slider 52. Thus, by forcing the slider 52 to slide relative to the operating section body 51, the operating wire 21 is allowed to be advanced or retracted relative to the needle pipe 10. As the operating section body 51 is displaced relative to the sheath 40, the needle pipe 10 is advanced or retracted relative to the sheath 40, and a protrusion amount of the needle pipe 10 from a distal end of the sheath 40 can be adjusted.

With respect to an operation of the biopsy needle 1 of the present embodiment which is configured as described above when the biopsy needle 1 is used, the case of using a pancreas as tissue to be biopsied (hereinafter referred to simply as "target tissue") will be described by way of example.

First, an operator introduces an endoscope (not shown) into a body of a patient, and displaces a distal end section of the endoscope up to the vicinity of the pancreas. Next, the operator inserts the biopsy needle 1 into a forceps channel of the endoscope from the side of the piercing section 11 with the needle pipe 10 being housed in the sheath 40, and causes a distal end section of the sheath 40 to protrude from a distal end opening of the forceps channel. The endoscope used may be appropriately selected from various known endoscopes such as an optical endoscope and an ultrasonic endoscope depending on a type or a position of the target tissue.

The operator operates the operating section body 51 to cause the piercing section 11 to protrude from the sheath 40 while checking the pancreas and a portion to collect a tissue segment of the pancreas by an image of the endoscope, and also inserts the piercing section 11 into the pancreas.

When the piercing section 11 reaches a target position, the operator pulls the slider 52. Thereby, the operating wire 21 connected to the slider 52 is retracted relative to the needle pipe 10, and, as shown in FIG. 3, the collection member 13 is rotated around the rotation shaft 15 such that the pin 16 moves toward a proximal end thereof. As a result, the cup section 14 moves outside the needle pipe 10 from the side hole 12, and a part of the pancreas Pc is cut off by the periphery 14A and is stored in the storage space of the cup section 14. If the tissue is hard or the like, the operator may resect a part of the pancreas Pc by repeating the advance or retraction of the slider 52 several times as needed or combining a retracting operation of the needle pipe 10 itself.

After the above operation, the operator advances the slider 52. Then, the cup section 14 enters from the side hole 12 into the needle pipe 10 again, and the resected tissue segment is also housed in the needle pipe 10. The operator retracts the needle pipe 10 to remove the needle pipe 10 from the pancreas Pc, and houses the needle pipe 10 in the sheath 40. Afterwards, the operator removes the biopsy needle 1 from the endoscope, and collects the tissue segment inside the cup section 14.

According to the biopsy needle 1 of the present embodiment, since the collection member 13 is mounted in the needle pipe 10 such that the opening of the cup section 14 is directed to the side hole 12 of the needle pipe 10, the moment the periphery 14A of the cup section 14 which is formed in a cutting edge shape moves outside the needle pipe 10, the periphery 14A comes into contact with the target tissue, and begins to cut the target tissue. Accordingly, an operation for collecting the tissue is easy without the need to cause the cup section to greatly protrude from the needle pipe within the tissue before the tissue is collected.

Further, the cup section 14 protrudes outside the needle pipe 10 when the slider 52 is retracted to pull the operating wire 21 toward the proximal end of the needle pipe 10. Since the operating wire 21 is highly resistant to tension, a force caused by the traction can be suitably transmitted to the collection member. As a result, the tissue can be collected by suitably displacing the cup section 14 outside the needle pipe 10 against the tissue present around the needle pipe 10.

Second Embodiment

Figure 5:
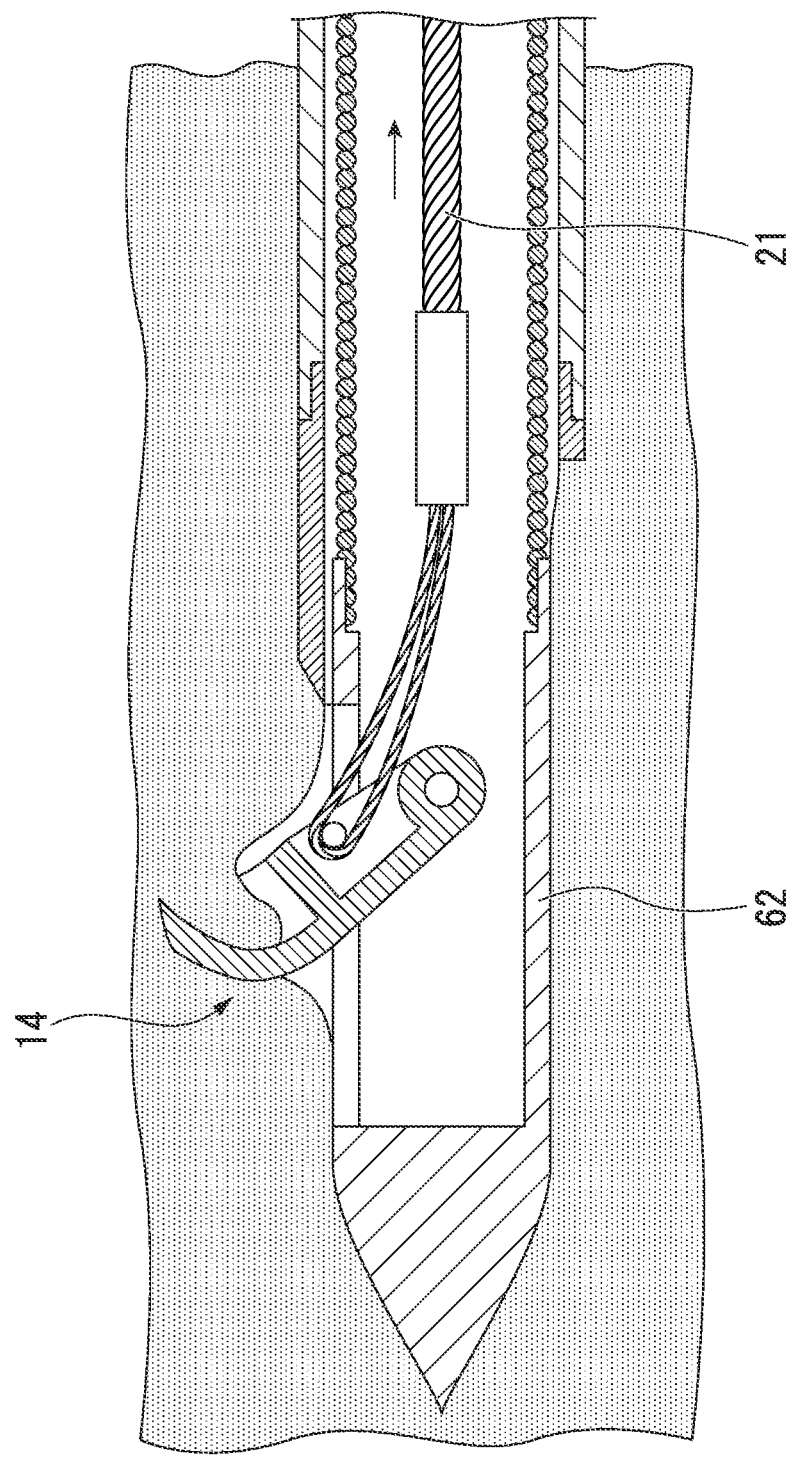
FIG. 5 is a view showing an operation of the biopsy needle in use.
Figure 6:
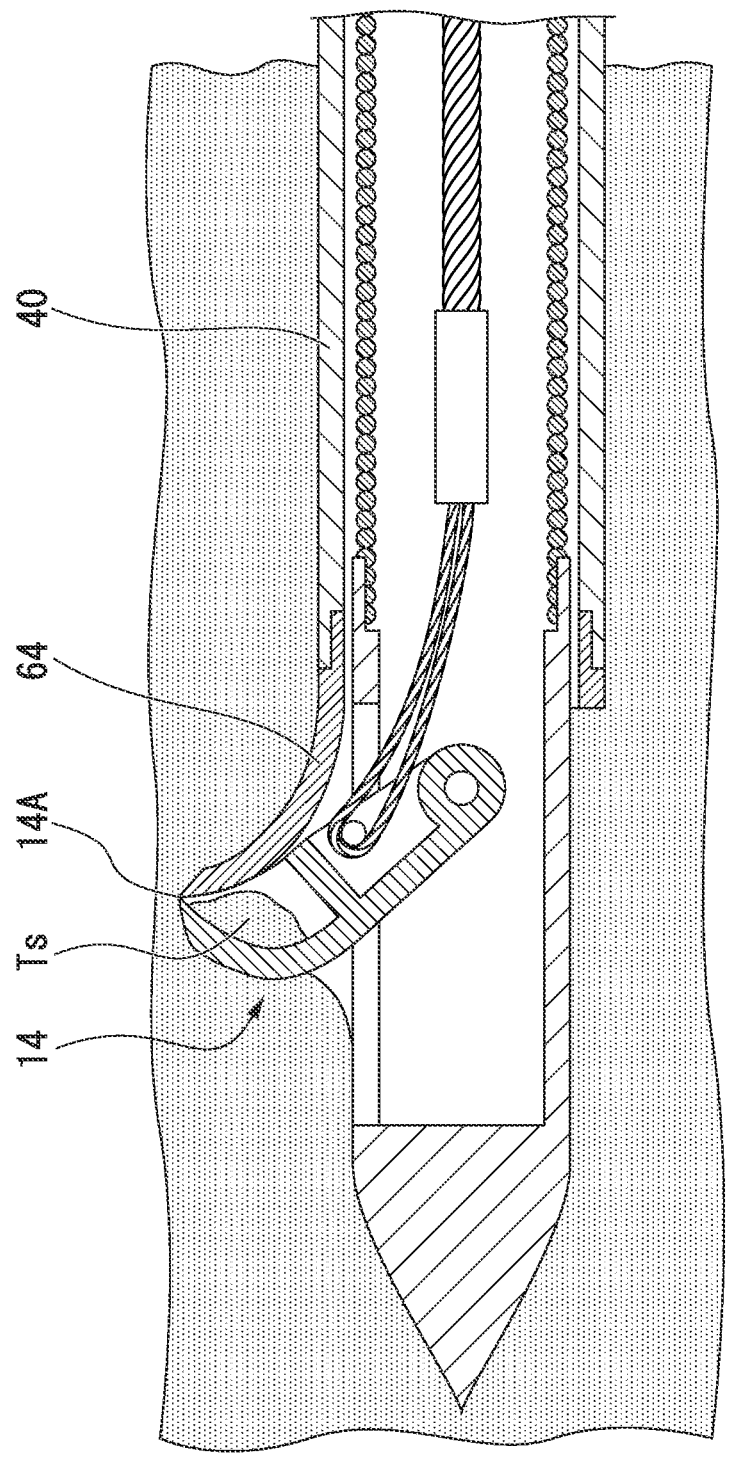
FIG. 6 is a view showing an operation of the biopsy needle in use.

Next, a second embodiment of the present invention will be described with reference to FIGS. 4 to 6. A biopsy needle 61 of the present embodiment is different from the biopsy needle 1 of the aforementioned first embodiment in that the biopsy needle 61 further includes an outer blade. In the following description, components that are in common with the previously described components are given the same reference numerals, and a repeated description thereof will be omitted here.

Figure 4:
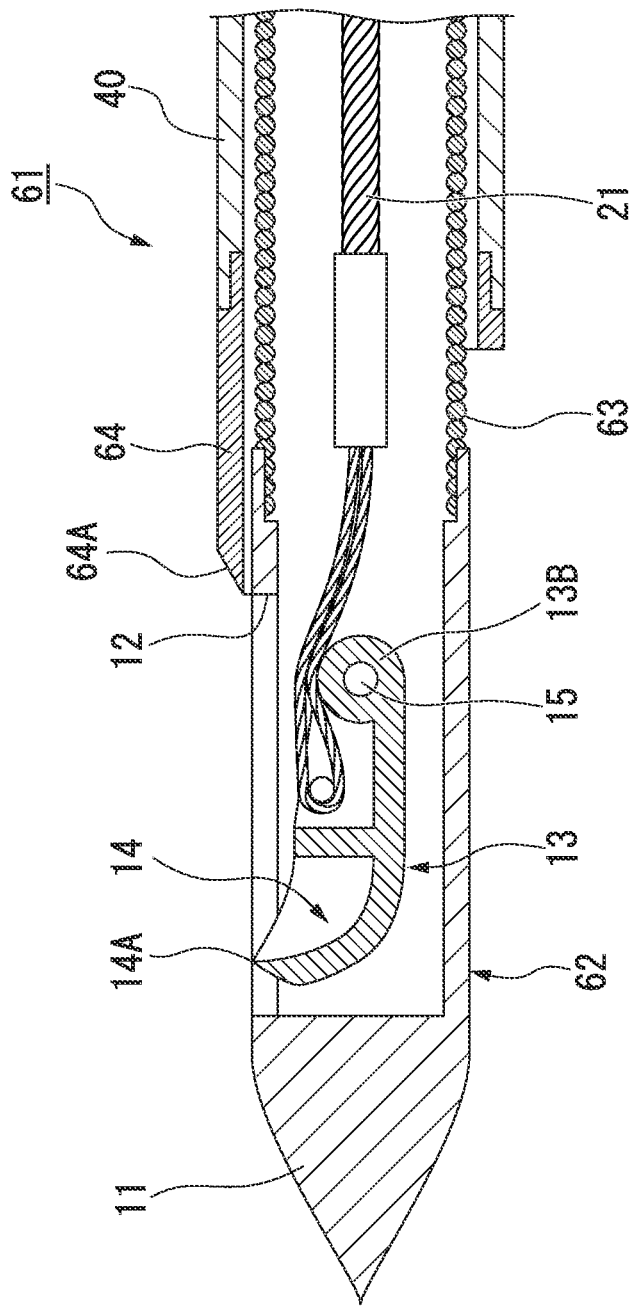
FIG. 4 is a cross-sectional view of a distal end section of a needle pipe and surroundings thereof in a biopsy needle of a second embodiment of the present invention.

FIG. 4 is a cross-sectional view showing a piercing section of the biopsy needle 61 and surroundings thereof. A needle pipe 62 of the biopsy needle 61 is configured such that only a piercing section 11 and the periphery of a side hole 12 are formed of a hollow metal member and a coil 63 is connected to the side of a proximal end thereof. An outer blade 64 for assisting with collection of a tissue segment is mounted on a distal end of a sheath 40.

The outer blade 64 is formed of a material such as a metal in a gutter shape or a half pipe shape having approximately the same diameter as the sheath 40. A sharp cutting edge section 64A is formed at a tip of the outer blade 64. A position of the cutting edge section 64A in a circumferential direction of the needle pipe 62 is approximately the same as positions of the side hole 12 and an opening of the cup section 14.

An operation of the biopsy needle 61 configured as described above when the biopsy needle 61 is used will be described. An operation of pulling the operating wire 21 to displace the cup section 14 outside the needle pipe 62 as shown in FIG. 5 is the same as in the first embodiment. After the traction of the operating wire 21, an operator grasps a proximal end section of the sheath 40, and advances the sheath 40 relative to the operating section body 51, or retracts the needle pipe 62 relative to the sheath 40. Then, as shown in FIG. 6, the outer blade 64 is advanced toward the cup section 14, and the cutting edge section 64A cuts target tissue Ts from the opposite side of the periphery 14A of the cup section 14. The target tissue Ts cut by the periphery 14A and the outer blade 64 is stored in the cup section 14 as a tissue segment.

Like the biopsy needle 1 of the first embodiment, the biopsy needle 61 of the present embodiment can also be easily operated to suitably collect the tissue. Further, since the outer blade 64 is provided in the sheath 40, even when the tissue cannot be sufficiently cut by the cup section alone, the outer blade can assist in cutting the tissue to reliably collect the tissue.

Third Embodiment

Next, a third embodiment of the present invention will be described with reference to FIGS. 7 to 9. A difference between a biopsy needle 71 of the present embodiment and the biopsy needle of each of the aforementioned embodiments is a shape of the collection member.

Figure 7:
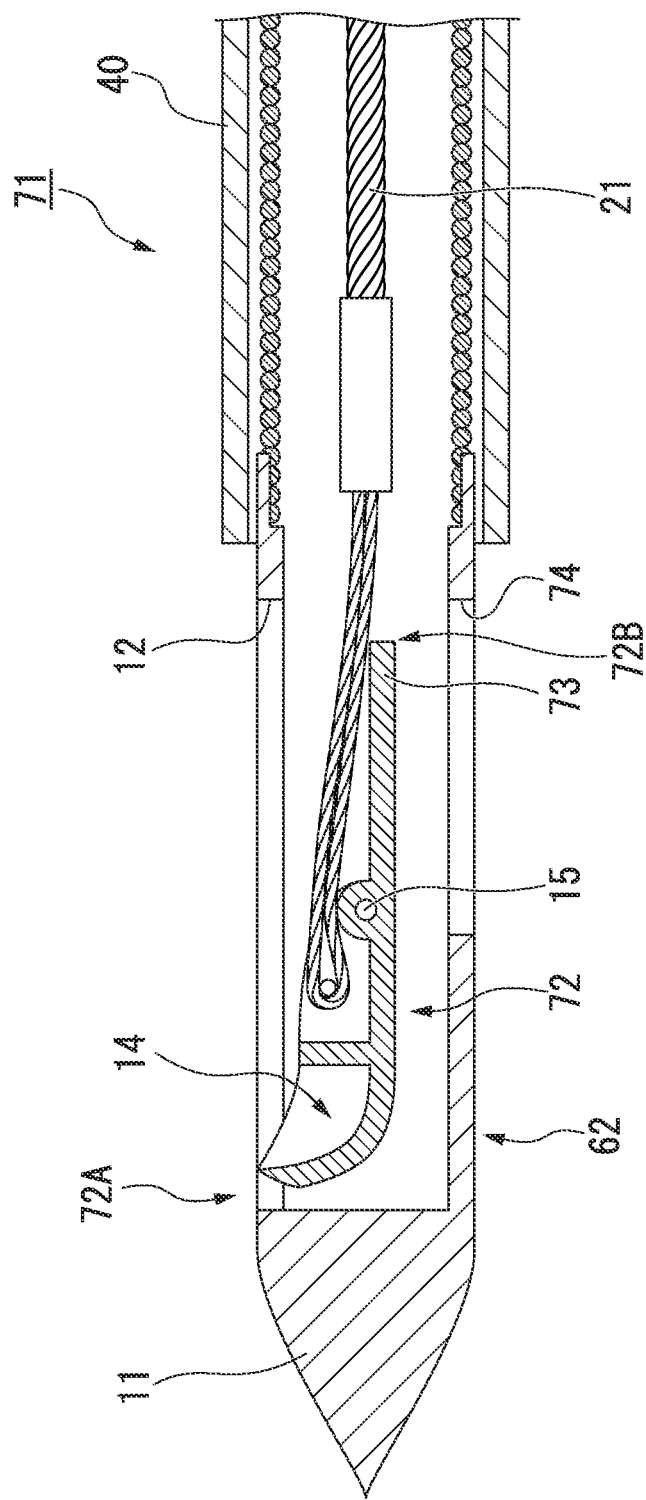
FIG. 7 is a cross-sectional view of a distal end section of a needle pipe and surroundings thereof in a biopsy needle of a third embodiment of the present invention.

FIG. 7 is a cross-sectional view showing a piercing section of the biopsy needle 71 and surroundings thereof. Like the collection member 13, a collection member 72 has a cup section 14 formed at a first end 72A in a longitudinal direction thereof. A second end 72B located on the opposite side of the first end 72A is provided with a protrusion section 73 formed in a bar shape or a plate shape.

A longitudinal middle section of the collection member 72 is supported on a needle pipe 62 by a rotation shaft 15. A second side hole 74 communicating with an inner cavity is formed in an outer circumferential surface of the needle pipe 62 at a proximal end side relative to the rotation shaft 15. When the collection member 72 rotates around the rotation shaft 15, the protrusion section 73 protrudes from the second side hole 74.

Figure 8:
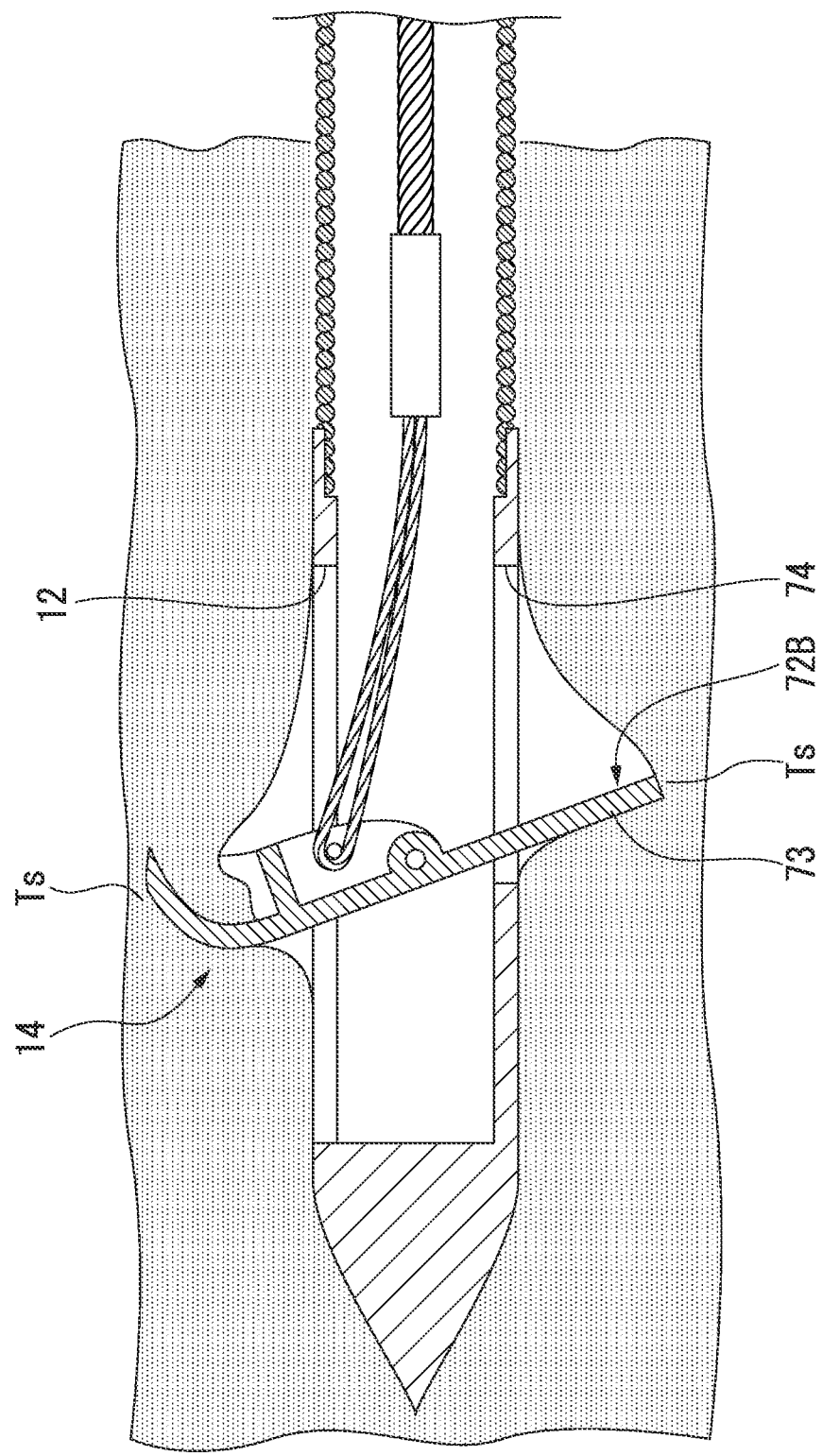
FIG. 8 is a view showing an operation of the biopsy needle in use.
Figure 9:
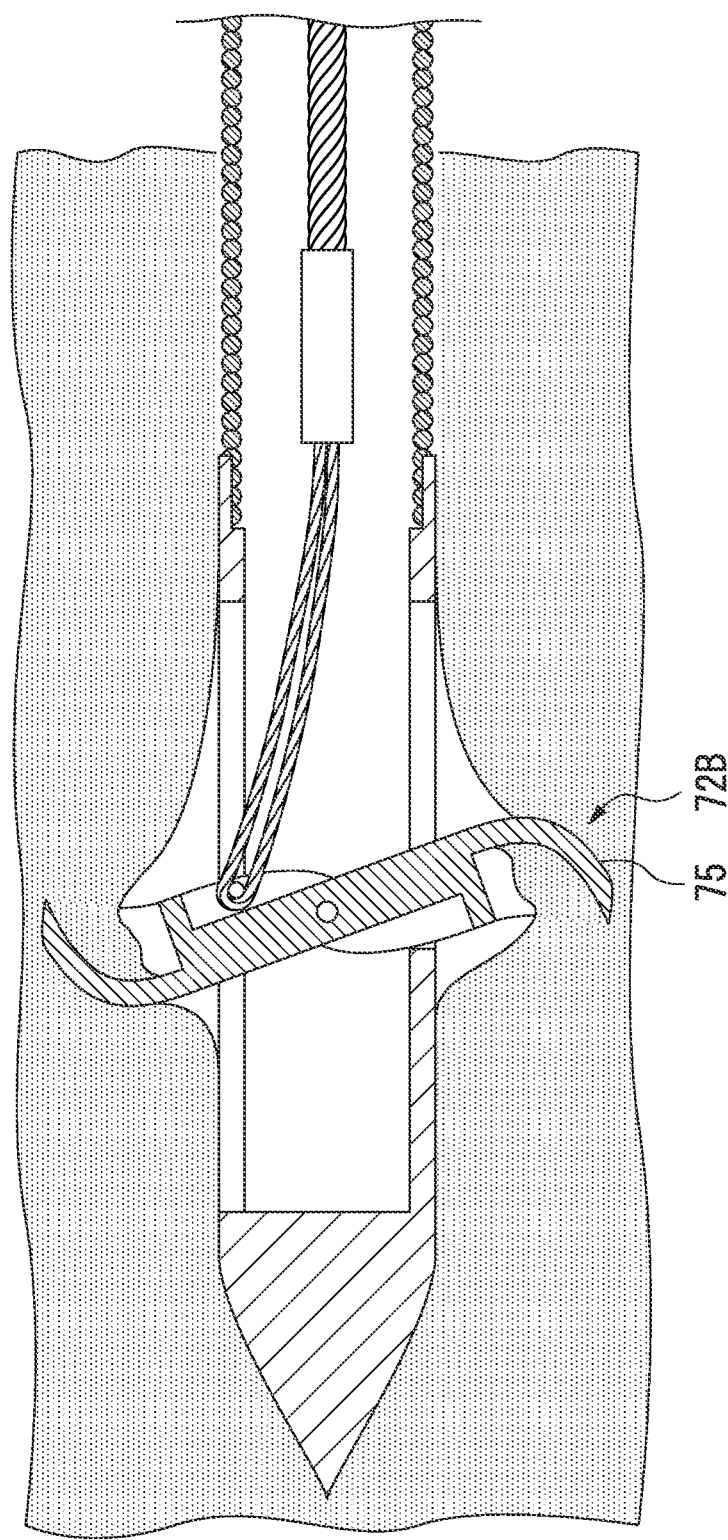
FIG. 9 is a view showing a modified example of the biopsy needle.

In the biopsy needle 71 formed as described above, when an operator pulls an operating wire 21, the cup section 14 protrudes from a side hole 12 in the same movement as in the first embodiment, as shown in FIG. 8. In this case, the protrusion section 73 provided in the second end 72B also protrudes outside the needle pipe 62 from the second side hole 74. The protrusion section 73 protruding outside the needle pipe 62 presses its surrounding target tissue Ts, and receives a reaction force from the target tissue Ts. Such a reaction force functions to press the cup section 14 against the target tissue Ts, and thus the tissue is stably collected by the cup section 14.

Like the biopsy needle of each of the embodiments, the biopsy needle 71 of the present embodiment can also be easily operated to suitably collect the tissue. Further, since the second side hole 74 and the protrusion section 73 are provided, the cup section 14 can be suitably pressed against the target tissue Ts, and the tissue can be suitably collected.

In the present embodiment, the shape of the protrusion section is not limited to the bar shape or the plate shape. For example, as in a modified example shown in FIG. 9, a second cup section 75 functioning as the protrusion section may be formed at the second end 72B. In this constitution, with respect to one cup section (first cup section), the other cup section (second cup section) functions as the protrusion section (i.e., the cup section (first cup section) 14 functions as the protrusion section with respect to the second cup section 75). Thus, the tissue can be suitably collected by the two cup sections.

Fourth Embodiment

Next, a fourth embodiment of the present invention will be described with reference to FIGS. 10 to 12. A difference between a biopsy needle 81 of the present embodiment and the biopsy needle of each of the aforementioned embodiments is a connecting method between the collection member and the operating member.

Figure 10:
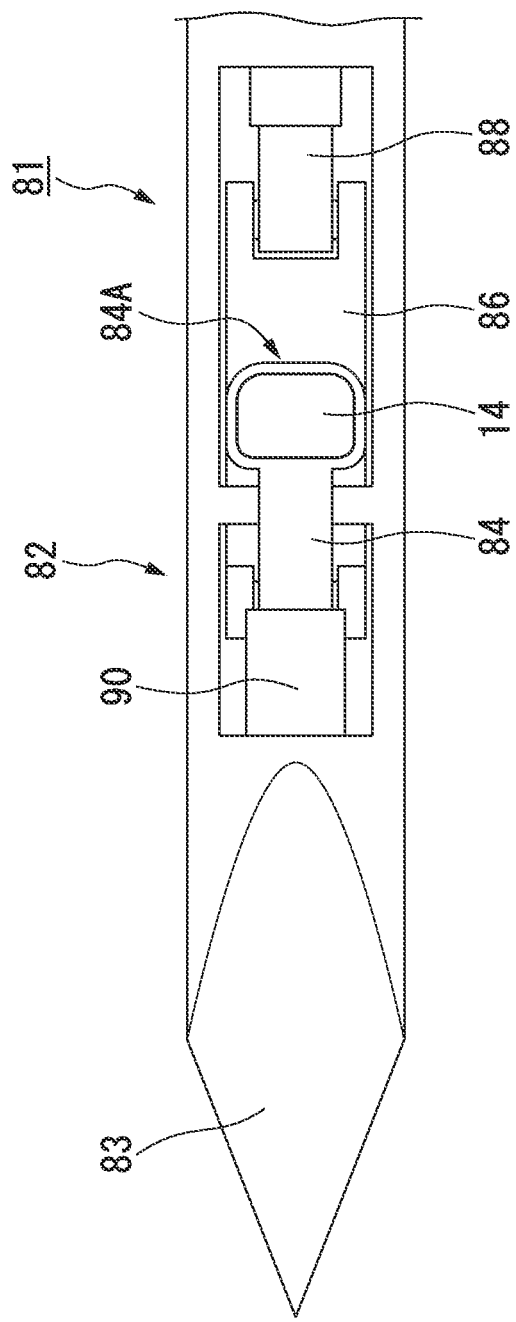
FIG. 10 is a plan view of a distal end section of a needle pipe and surroundings thereof in a biopsy needle of a fourth embodiment of the present invention.
Figure 11:
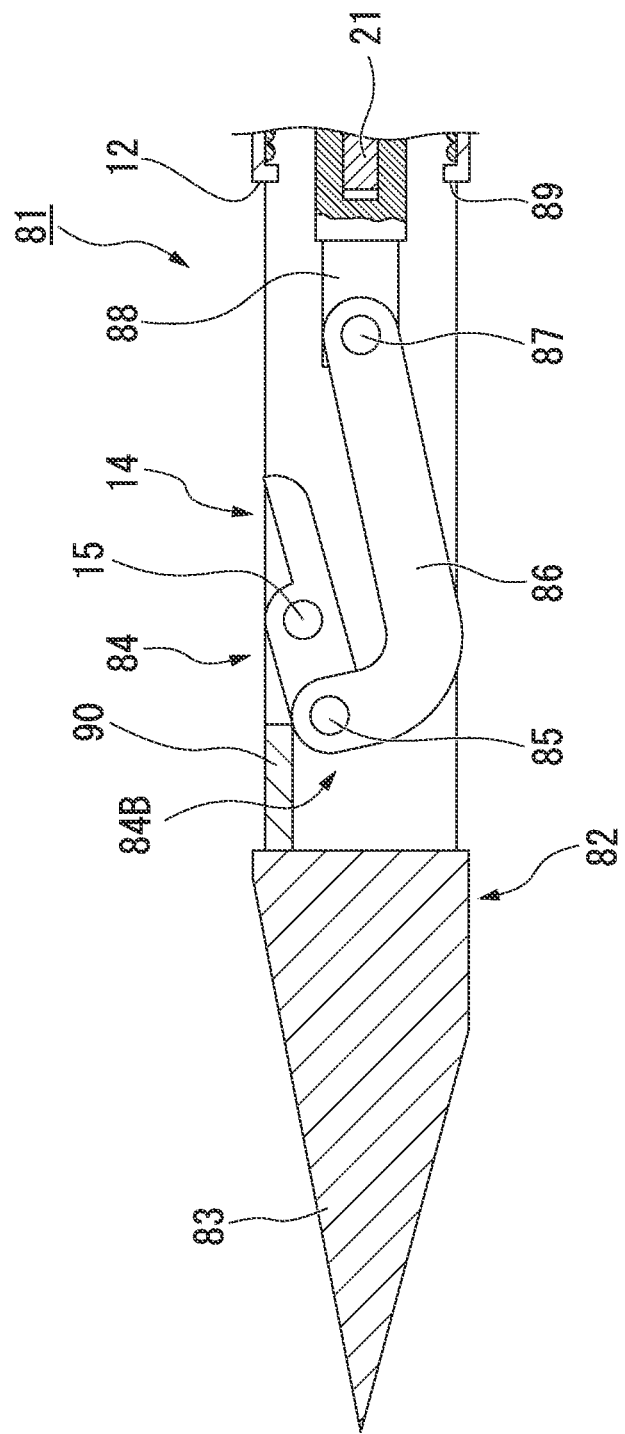
FIG. 11 is a view showing the distal end section of the needle pipe and surroundings thereof in a partial cross section.

FIG. 10 is a plan view showing a piercing section of the biopsy needle 81 and surroundings thereof, and FIG. 11 is a side view showing the same portions in a partial cross section. In the biopsy needle 81, the piercing section 83 of a needle pipe 82 is sharply formed by cutting off an outer circumferential surface of a distal end at four places equally spaced in a circumferential direction obliquely with respect to a central axis.

A collection member 84 is mounted in the needle pipe 82 such that a first end 84A in which a cup section 14 is provided is located at the side of a proximal end of the needle pipe 82. A second end 84B of the collection member 84 is provided with a link pin 85, and a front end of a link 86 having a plate shape or a bar shape is mounted to be rotatable around the link pin 85.

As shown in FIG. 11, a connecting member 88 having a link shaft 87 is mounted on a distal end of the operating wire 21, and a rear end section of the link 86 is mounted to be rotatable around the link shaft 87. The needle pipe 82 is provided with a second side hole 89 that communicates with an inner cavity and prevents interference with the link 86.

A cutting section 90 having a plate shape is provided between the piercing section 83 and the collection member 84, and the cup section 14 of the collection member 84 rotating around the rotation shaft 15 can come into contact with the cutting section 90.

Figure 12:
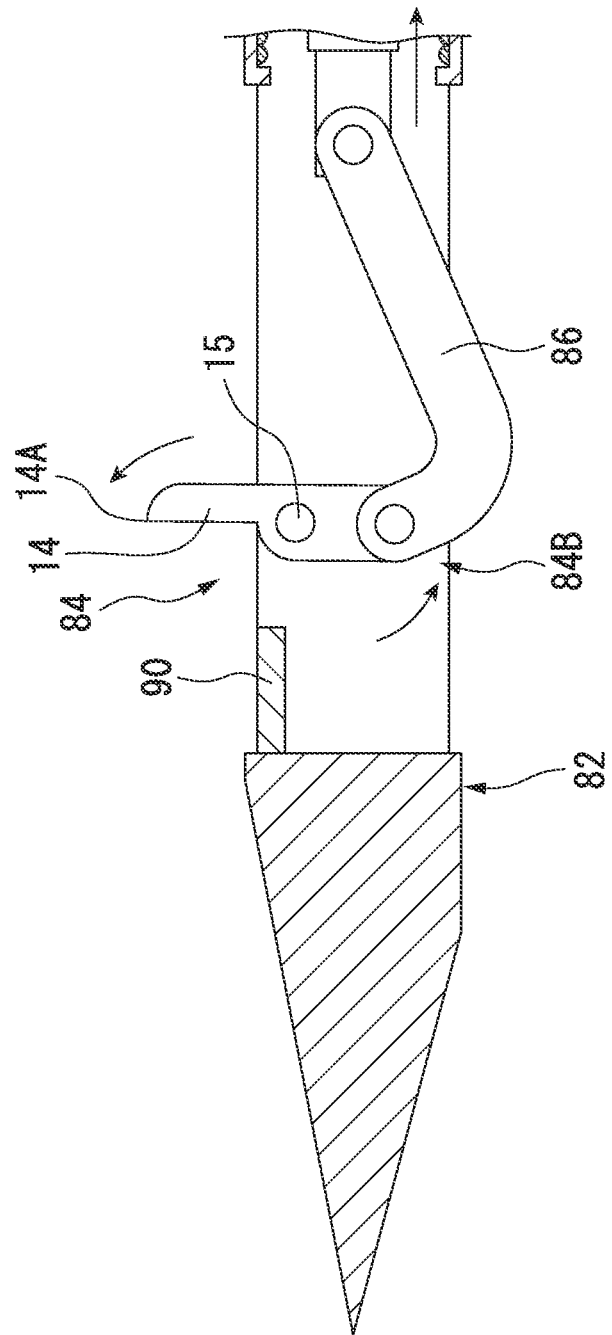
FIG. 12 is a view showing an operation of the biopsy needle in use.

In the biopsy needle 81 of the present embodiment, when an operator pulls the operating wire 21, the second end 84B of the collection member 84 is displaced to the proximal end side while the link 86 moves to the proximal end side as shown in FIG. 12. As a result, the collection member 84 rotates around the rotation shaft 15, and the cup section 14 protrudes outside the needle pipe 82 while moving from the proximal end side toward the distal end side, and cuts target tissue. When the operator further pulls the operating wire 21, a periphery 14A of the cup section 14 is pressed against the cutting section 90, and the target tissue is cut by the periphery 14A. A part of the cut target tissue is housed in the cup section 14 as a tissue segment.

Like the biopsy needle of each of the aforementioned embodiments, the biopsy needle 81 of the present embodiment can also be easily operated to suitably collect the tissue. Further, since the collection member 84 and the operating wire 21 are connected via the link 86, a rotating range of the collection member can be further increased at an angle of, for instance, about 150 degrees, and the tissue is more easily cut.

In the present embodiment, the example in which the cup section 14 is rotated toward the distal end side has been described, but the cup section may be configured to be rotated toward the proximal end. In this case, a direction of the opening of the cup section may be opposite to a direction shown in FIG. 10, and the operating wire 21 may be operated to be advanced from a completely pulled state. However, as described above, since the operating wire has good force transmissibility based on the pulling operation, a structure in which the cup section is rotated toward the distal end is preferable in that it can collect the tissue with a greater force.

Further, in the present embodiment, the cutting section is not essential. For example, without providing the cutting section, the collection member may be configured to be sufficiently rotated to cut the tissue. In this case, the collection member may be sufficiently rotated, and the periphery of the cup section that once protrudes outside the needle pipe may be displaced into the needle pipe again, thereby improving cutting ability.

Although embodiments of the present invention have been described, the technical scope of the present invention is not limited to the aforementioned embodiments. Without departing from the scope of the present invention, a combination of the components may be changed, or each component may be modified in various ways or be eliminated.

Figure 13:
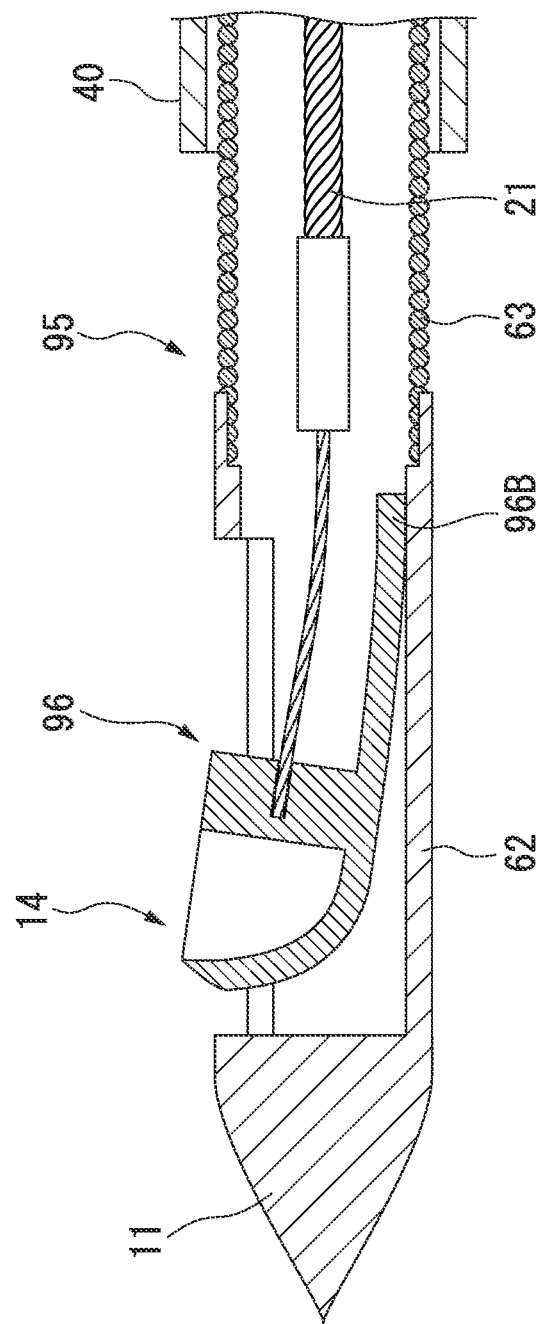
FIG. 13 is a cross-sectional view of a distal end section of a needle pipe and surroundings thereof in a biopsy needle of a modified example of the present invention.
Figure 14:
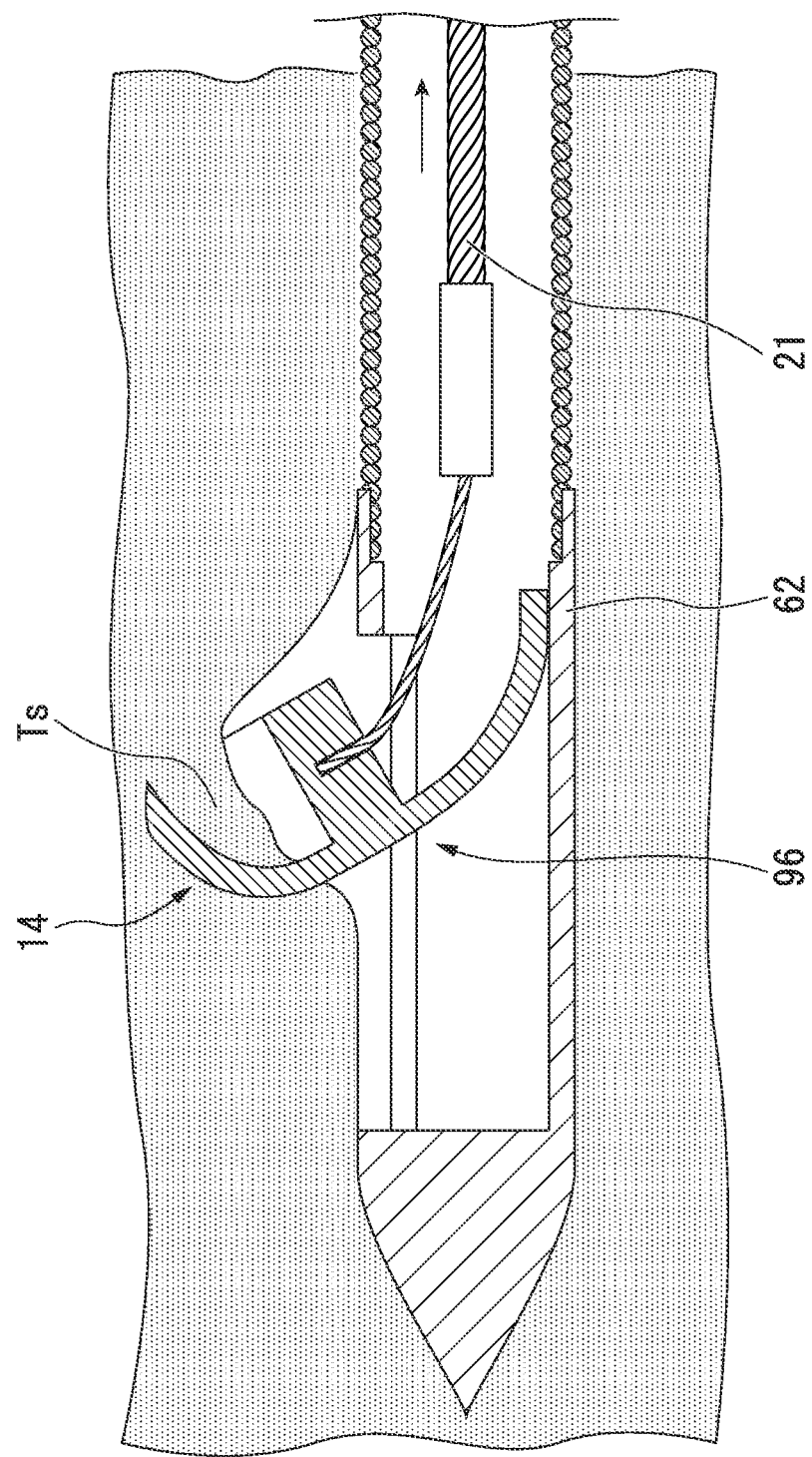
FIG. 14 is a view showing an operation of the biopsy needle in use.

For example, in the treatment device for an endoscope of the present invention, the collection member may not necessarily be mounted in the needle pipe via the rotation shaft. In FIGS. 13 and 14, a biopsy needle 95 of such a modified example is shown. In the biopsy needle 95, a second end 96B of a collection member 96 is formed in a plate shape, and is fixed to an inner surface of a needle pipe 62 by such as welding or brazing without the rotation shaft. An operating wire 21 is connected to a proximal end side of a cup section 14.

In the biopsy needle 95, when an operator pulls the operating wire 21, a plate-shaped region of the collection member 96 which is located at the proximal end side relative to the cup section 14 is bent as shown in FIG. 14. Thereby, the cup section 14 moves outside the needle pipe 62 to resect target tissue Ts. This constitution can also produce the same effects as the biopsy needle of each of the aforementioned embodiments.

The present invention is not to be considered as being limited by the foregoing description, and is only limited by the scope of the appended claims.

What is claimed is:

1. A medical device for an endoscope comprising:
   a needle pipe having flexibility and formed in an elongated shape;
   a hollow shape section having an inner cavity formed in a distal end section of the needle pipe, and a side hole that is formed on an outer side surface of the needle pipe and communicates with the inner cavity;
   a piercing section provided closer to a distal end side of the needle pipe than the hollow shape section and formed with a pointed tip;
   a collection member including a cutting edge section that is formed in a pointed shape toward a radial outer direction of the needle pipe and is configured to protrude and retract between a position at which the cutting edge section is housed in the hollow shape section and a position at which the cutting edge section protrudes from the side hole;
   an operating member including a distal end portion connected to the collection member, the operating member being provided so as to be advanceable and retractable relative to the needle pipe;
   a sheath into which the needle pipe is inserted so as to be advanceable and retractable; and
   an outer blade provided at a distal end section of the sheath and configured to cut tissue collected by the collection member, wherein
   the cutting edge section protrudes from the side hole when the operating member is displaced relative to the needle pipe.

2. The medical device according to claim 1, wherein
   the collection member includes a cup section having an opening to a storage space capable of storing tissue therein,
   the cutting edge section is formed in a periphery of the opening, and
   the opening opens toward the side hole in a state in which the cup section is housed in the hollow shape section.

3. The medical device according to claim 1, further comprising
   a link that connects the collection member and the operating member, wherein the collection member is mounted in the needle pipe via a rotation shaft, and is rotatable around the rotation shaft.

4. A medical device for an endoscope comprising:
   a needle pipe having flexibility and formed in an elongated shape;
   a hollow shape section having an inner cavity formed in a distal end section of the needle pipe, and a side hole that is formed on an outer side surface of the needle pipe and communicates with the inner cavity;
   a piercing section provided closer to a distal end side of the needle pipe than the hollow shape section and formed with a pointed tip;
   a collection member including a cutting edge section that is formed in a pointed shape toward a radial outer direction of the needle pipe and is configured to protrude and retract between a position at which the cutting edge section is housed in the hollow shape section and a position at which the cutting edge section protrudes from the side hole; and an operating member including a distal end portion connected to the collection member, the operating member being provided so as to be advanceable and retractable relative to the needle pipe, wherein the cutting edge section protrudes from the side hole when the operating member is displaced relative to the needle pipe, the collection member is mounted in the needle pipe via a rotation shaft, and is rotatable around the rotation shaft, the collection member includes a first cup section, which is mounted in the needle pipe via the rotation shaft and is rotatable around the rotation shaft, at a first end of the collection member in a longitudinal direction of the collection member, and a middle section of the collection member in the longitudinal direction is supported on the rotation shaft, and when the operating member is retracted relative to the needle pipe, a second end of the collection member in the longitudinal direction protrudes from a second side hole formed in the needle pipe.

5. The medical device according to claim 4, wherein the collection member further includes a second cup section that is provided at the second end of the collection member and opens toward a radial outer side of the needle pipe.

6. The medical device according to claim 2, further comprising a cutting section which is provided in the needle pipe and with which the rotated cup section comes into contact.

\* \* \* \* \*